(12) United States Patent
Tao et al.

(10) Patent No.: US 10,935,496 B2
(45) Date of Patent: Mar. 2, 2021

(54) COLLOIDAL METASURFACE SENSORS AND ENHANCED RAMAN SPECTROSCOPY METHODS

(71) Applicant: The Regents of the University of California, Oakland, CA (US)

(72) Inventors: Andrea Tao, La Jolla, CA (US); Tyler Dill, La Jolla, CA (US); Andrea Rodarte, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 19 days.

(21) Appl. No.: 16/387,748

(22) Filed: Apr. 18, 2019

(65) Prior Publication Data

US 2019/0323967 A1    Oct. 24, 2019

Related U.S. Application Data

(60) Provisional application No. 62/659,286, filed on Apr. 18, 2018.

(51) Int. Cl.
*G01N 21/65* (2006.01)
*G02B 1/00* (2006.01)
*G01N 21/25* (2006.01)

(52) U.S. Cl.
CPC .......... *G01N 21/658* (2013.01); *G01N 21/25* (2013.01); *G02B 1/002* (2013.01); *G01N 2021/258* (2013.01)

(58) Field of Classification Search
CPC ................. G01N 21/658; G01N 21/25; G01N 2021/258; G02B 1/002
See application file for complete search history.

(56) References Cited

U.S. PATENT DOCUMENTS

| | | | |
|---|---|---|---|
| 2008/0266555 A1* | 10/2008 | Murphy | B82Y 30/00 356/301 |
| 2012/0105841 A1* | 5/2012 | Hu | G01J 3/44 356/301 |
| 2015/0126388 A1* | 5/2015 | Kong | G01N 33/532 506/9 |
| 2017/0045456 A1* | 2/2017 | Fabris | G01N 21/658 |
| 2018/0231418 A1* | 8/2018 | Park | C23C 16/0236 |

OTHER PUBLICATIONS

Dill, Tyler J., et al. "Investigating the effect of Ag nanocube polydispersity on gap-mode SERS enhancement factors." Analyst 141.12 (2016): 3916-3924, (Year: 2016).*

Suh, Yang-won, et al. "UVA/B-induced formation of free radicals from decabromodiphenyl ether." Environmental science & technology 43.7 (2009): 2581-2588 (Year: 2009).*

(Continued)

*Primary Examiner* — Dominic J Bologna
(74) *Attorney, Agent, or Firm* — Greer, Burns & Crain. Ltd.; Steven P. Fallon (57) ABSTRACT

A chemical analyte sensor. The sensor has a monolayer of shaped nanostructures, a metal or metallized surface, and analyte confined between the monolayer of shaped nanostructures and the metal or metallized surface. The analyte is confined in the highly absorbing optical cavity of the metasurface defined at the metal or metallized surface.

18 Claims, 14 Drawing Sheets

(56) References Cited

OTHER PUBLICATIONS

Sun, Zhenli, et al. "Rapid detection of 2, 2', 4, 4'-tetrabromodiphenyl ether (BDE-47) using a portable Au-colloid SERS sensor." Journal of Raman Spectroscopy 45.9 (2014): 745-749 (Year: 2014).*

Huong et al, "Adsorption of Bromide Ions on Single Crystals of Gold: Determination of Thermodynamic Parameters and Electroreflectance Investigations", J. Electroanal. Chem., 1983, pp. 149-162, vol. 151, Elsevier Sequoia S.A.

Jiang et al, "Surface-enhanced Raman spectroscopy detection of polybrominated diphenylethers using a portable Raman spectrometer", Talanta, 2013, pp. 14-17, vol. 116, Elsevier B.V.

Man et al., "Cancer risk assessment of polybrominated diphenyl ethers (PBDEs) and polychlorinated biphenyls (PCBs) in former agricultural soils of Hong Kong", Journal of Hazardous Materials, 2011, pp. 92-99, vol. 195, Elsevier B.V.

Nikoobakht et al, "Surface-enhanced Raman scattering of molecules adsorbed on gold nanorods: off-surface plasmon resonance condition", Chemical Physics Letters, 2002, pp. 17-23, vol. 366, Elsevier Science B.V.

Patterson et al., "Surface-Enhanced Raman Spectroscopy as a Probe of Adsorbate-Surface Bonding: Simple Alkenes and Alkynes Adsorbed at Gold Electrodes", The Journal of Physical Chemistry, 1985, pp. 5046-5051, vol. 89, vol. 23, American Chemical Society.

Sun et al., "Rapid detection of 2,2',4,4'-tetrabromodiphenyl ether (BDE-47) using a portable Au-colloid SERS sensor", Journal of Raman Spectroscopy, 2014, pp. 745-749, vol. 45, John Wiley & Sons, Ltd.

Zhuang et al., "Debromination of Polybrominated Diphenyl Ethers by Nanoscale Zerovalent Iron: Pathways, Kinetics, and Reactivity", Environmental Science and Technology, 2010, pp. 8236-8242, vol. 44, No. 21, American Chemical Society.

* cited by examiner

Alkane Thiol functionalized Au

FIG. 9B ent sensor; FIG. 1B schematically illustrates a debromi-

COLLOIDAL METASURFACE SENSORS AND ENHANCED RAMAN SPECTROSCOPY METHODS

PRIORITY CLAIM AND REFERENCE TO RELATED APPLICATION

The application claims priority under 35 U.S.C. § 119 from prior provisional application Ser. No. 62/659,286, which was filed Apr. 18, 2018.

FIELD

Fields of the invention include chemical sensors, metamaterials and Raman spectroscopy. Example applications of the invention include sensing for chemicals. Particular preferred applications include chemical sensing in waste water and for detection of halogenated soil contaminants. An additional example application includes sensing for Polybrominated diphenyl ethers (PBDEs) in drinking water or breast milk.

BACKGROUND

Contaminants are sometimes difficult to detect and can be present in critical liquids consumed by humans, or in materials that are discharged in the environment. Such difficult-to-detect contaminants include PDBEs in liquids consumed by humans and halogenated soil contaminants PBDEs are a common brominated flame retardant, and are commonly found in consumer products. Because they are not chemically bound to polymers, PBDEs are blended in during formation and have the ability to migrate from products into the environment. Zhuang, Y.; Ahn, S.; Luthy, R. G., "Debromination of Polybrominated Diphenyl Ethers by Nanoscale Zerovalent Iron: Pathways, Kinetics, and Reactivity," *Environ. Sci. Technol.* 2010, 44, 8236-8242. Studies suggest that PBDEs pose potential health risks as hormone disruptors, adverse neurobehavioral toxins and as a cause of reproductive or developmental effects. Man, Y. B.; Lopez, B. N.; Wang, H. S.; Leung, A. O. W.; Chow, K. L.; Wong, M. H., "Cancer risk assessment of polybrominated diphenyl ethers (PBDEs) and polychlorinated biphenyls (PCBs) in former agricultural soils of Hong Kong. *Journal of Hazardous Materials* 2011, 195, 92-99. Due to the risks, the detection of PBDEs even in low concentrations is important. Previous studies have exploited the hydrophobic nature of PBDEs by functionalizing nanoparticles with alkane thiol ligands or by optimizing the concentration of citrate content in the sampling solution. Jiang, X.; Lai, Y.; Wang, W.; Jiang, W.; Zhan, J., "Surface-enhanced Raman spectroscopy detection of polybrominated diphenylethers using a portable Raman spectrometer," *Talanta* 2013, 116, 14-17; Sun, Z.; Du, J.; Yan, L.; Jing, C., "Rapid detection of 2,2',4,4'-tetrabromodiphenyl ether (BDE-47) using a portable Au-colloid SERS sensor," *J. Raman Spectrosc.* 2014, 45, 745-749.

Analytical methods used for PBDE detection include gas chromatography (GC)-mass spectrometry (MS) for air, sewage, fish and animal tissues; capillary column GC/electron capture detector (ECD) for water and sediment samples; GC/high resolution MS (HRMS) for fish tissue; and liquid chromatography (LC)-GC-MS/flame ionization detector (FID) for sediments (ATSDR 2015).

The strongest observed SERS (surface enhanced spectroscopy) peaks associated with PBDEs tend to be attributed to the skeletal stretching or ring modes of the molecule. These modes are problematic when attempting to identify a fingerprint of PBDEs in the presence of other organic materials because the signature is not unique. Previous studies have shown that PBDEs will debrominate when exposed to UV radiation. When a solution of PBDEs is debrominated in the presence of a gold substrate, the negative bromide ion will be attracted to the gold surface (Nguyen Van Huong, C.; Hinnen, C.; Rousseau, A. Adsorption of bromide ions on single crystals of gold: Determination of thermodynamic parameters and electroreflectance investigations. *Journal of Electroanalytical Chemistry and Interfacial Electrochemistry* 1983, 151, 149-162) and form an Au—Br bond that can be observed via SERS. The Au—Br stretch is observed at 175-180 $cm^{-1}$ which is distinct from the modes attributed to benzene rings. See, Nikoobakht, B.; Wang, J.; El-Sayed, M. A., "Surface-enhanced Raman scattering of molecules adsorbed on gold nanorods: off-surface plasmon resonance condition," *Chemical Physics Letters* 2002, 366, 17-23; Gao, P.; Weaver, M. J., "Surface-enhanced Raman spectroscopy as a probe of adsorbate-surface bonding: simple alkenes and alkynes adsorbed at gold electrodes," *J. Phys. Chem.* 1985, 89, 5046-5051.

SUMMARY OF THE INVENTION

An embodiment of the invention is a chemical analyte sensor. The sensor has a monolayer of shaped nanostructures, a metal or metallized surface, and analyte confined between the monolayer of shaped nanostructures and the metal or metallized surface. The analyte is confined in the highly absorbing optical cavity.

DETAILED DESCRIPTION OF THE PREFERRED EMBODIMENTS

Preferred embodiment sensors confine analyte in an optical cavity between a monolayer of shaped nanostructures and a metal or metallized surface to carry out surface enhanced Raman spectroscopy in a small confined volume but over a large area. A preferred sensor has a monolayer of shaped nanostructures, a metal or metallized surface, and analyte confined between the monolayer of shaped nanostructures and the metal or metallized surface. The analyte is confined in the highly absorbing optical cavity.

In a preferred method of fabrication, the sensor is fabricated using an elastomer stamp that is coated with a monolayer of functionalized metal nanostructures, e.g. functionalized Ag nanocubes. This stamp can then be applied onto the metal or metallized surface containing the desired analyte to form a sandwich-type structure, confining the analyte in a highly absorbing optical cavity and defining a metasurface in the region where the nanostructures are nearest the metal or metallized surface. Other nanostructures suitable for forming an optical cavity include nanodisks, nanoprisms, nanosheets, nanoribbons, nanopyramids, nanospheres, and nanorods.

A preferred metal surface is gold. Example nanostructured platform sensors of the invention provide signal-to-noise enhancements orders of magnitude better than existing art known to the inventors, which can be attributed to confinement of analyte in the optical cavity and the unique colloidal metasurface. Preferred sensing methods provide a molecule-specific vibrational signature via the collection of Raman scattered photons.

Various analytes can be detected. An analyte to be detected is physically confined in the optical cavity. Confinement can be carried out by physical entrapment of the analyte or through chemical interaction of the analyte with the shaped nanostructures or the metal or metallized surface. As an example, preferred sensors are able to detect low concentrations of Polybrominated diphenyl ethers (PBDEs) from aqueous solution. For the PBDEs entrapment is preferably achieved chemically via a bond to a metal or metallized surface. In an experiment, a solution of PBDE was exposed to UV light, which forms a bromine (Br) radical. Br then binds to a gold surface, which serves as the metal backplane for the metasurface. Detection leverages enhanced Raman spectroscopy—the nanostructured platform provides signal-to-noise enhancements orders of magnitude better than existing art due to the unique optical cavity and colloidal metasurface, and the sensors also provide molecule-specific vibrational signature via the collection of Raman scattered photons.

Many optical spectroscopy and imaging techniques are limited by the ability to fabricate nanoscale probes that are robust, reproducible, and support high quality optical resonances. Sensors of the invention with colloidal plasmonic metasurfaces defined with shaped nanostructure, e.g., nanoparticles, overcome these obstacles and enable sensitive spectroscopy and imaging. Present methods assemble a monolayer of colloidal nanoparticles on a metal or metallic surface to form a metasurface for second harmonic light generations and near-perfect light absorbers. Plasmonic nanodisks that are capable of upconverting near-infrared (NIR) light are another type of shaped nanostructure. Control of particle shape can be achieved by utilizing a single-source, supramolecular precursor that adopts liquid crystalline order, or by any known methods for forming a colloid of shaped nanostructures. Two-photon absorbing (TPA) inorganic nanoparticles can support plasmon resonances in the NIR to mid-infrared wavelengths, which can exhibit extraordinary two-photon action cross-sections.

Example experiments demonstrated highly sensitive detection. Nanostructured metasurface thin-film sensors were shown to detect low concentrations of Polybrominated diphenyl ethers (PBDEs) from aqueous solution. Solutions of concentrations of PBDE 15 varying from 1 nM to 1 mM in ethanol were prepared and a clean Au substrate treated with thiophenol was added to each vial. The samples, along with a prepared Au substrate in ethanol, were incubated under a 254 nm UV lamp for 3 hrs. After incubation, the samples were removed and dried and a PDMS stamp with thiophenol functionalized Ag nanocubes was placed on top. SERS measurements were taken using a 785 nm laser and data taken at 100 points on the surface were averaged. Measurements were taken using a Renishaw inVia microRaman. Raman spectra were collected in the range of 100-3400 wavenumbers.

Preferred embodiments of the invention will now be discussed with respect to the drawings and with respect to experiments that have been conducted to demonstrate the invention. The drawings may include schematic representations, which will be understood by artisans in view of the general knowledge in the art and the description that follows. Features may be exaggerated in the drawings for emphasis, and features may not be to scale. Artisans will understand broader aspects of the invention from the experiments and experimental data.

Figure 1A:
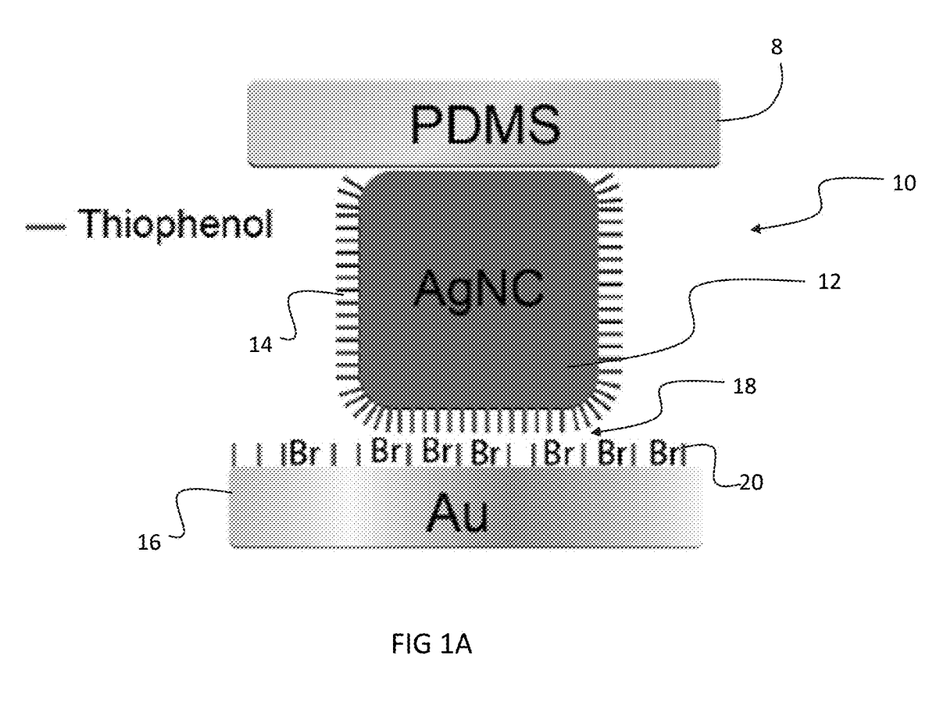
FIG. 1A is a schematic diagram of a preferred embodiment sensor.

FIG. 1A illustrates a preferred sensor and a method for forming the sensor with an elastomer stamp 8, such as polydimethylsiloxane PDMS stamp. The sensor includes a colloidal monolayer 10 of shaped nanostructures 12. For simplicity of illustration, one shaped nanostructure of the monolayer is shown in FIG. 1A, while the monolayer will extend to include additional shaped nanostructures, such as the example silver nanocube 12 shown in FIG. 1A. The shaped nanostructure has its surface functionalized with a layer 14 thiophenol. This layer 14 provides a known passivation layer for the nanostructure surface to protect and stabilize the nanostructure against contamination or degradation. The thiophenol also possesses a known and predetermined well-characterized Raman vibrational signature that is readily subtracted from spectral signatures, which eliminates background signal for data analysis. As metal or metallized surface 16 provides the ability to confine analyte between the monolayer 10 of shaped nanostructures 12 and the metal or metallized surface 16, for example a gold surface. The preferred metal for PBDE is gold as the Au—Br bond provides a convenient method for confinement of the PDBE analyte. Many other analytes can be confined and detected. One additional example is the detection of analytes such as 2D atomic crystals, e.g. graphene or h-BN. Simulation results show that other metals such as Ag, Fe, Ni, Pt, and Cu are suitable for the sensor. The analyte is confined in the highly absorbing optical cavity 18 in the region of the metasurface. The optical cavity 18 is formed in the gap between the metal or metallized surface 16 and the nanostructures 12, and can also extend into spaces between the nanostructures. FIG. 1A shows the metal or metalized surface 16 that binds a layer 20 of Br, which formed after degradation of the PBDE, prior to sensing. Br binds as a degradation of PBDE, but other binding techniques can be used. One or both of the metal or metallized surface 16 or the shaped nanostructures 12 can be functionalized to attract molecules of the analyte. Confinement can also be merely mechanical, by the sandwiching of the analyte between the monolayer 10 and the metal or metallized surface 16. The sensor of FIG. 1A can be fabricated by coating the elastomer stamp 8 with the monolayer 10 of shaped nanostructures 12. Analyte is attracted to the metal or metallized surface 16. The stamp 8 is then applied to the metal or metallized 16 to create the highly absorbing optical cavity 18. Analyte is confined in that optical cavity 18. Sensing is conducted by Raman scattering, which is collected at an oblique angle using a laser source that corresponds to the resonant excitation wavelength of the metasurface. The vibrational signatures of the analyte are analyzed from this signal. During signal collection, the optical excitation (i.e. the laser source used to illuminate the metasurface) must match or overlap with the optical resonance of the metasurface. For the experiential embodiment with Ag nanostructures on a gold surface, with the separation distance between the nanostructures and the gold is <10 nm and the size of the nanostructures is 50-100 nm, the optical resonance of the metasurface can be excited by a 785 nm laser. For a given sensor, the resonance of the metasurface can determined by taking a reflection spectrum of the metasurface and determining which wavelengths are highly absorbing. An acceptable range of wavelengths of the experimental sensors was determined to be 350-1100 nm.

Figure 1B:
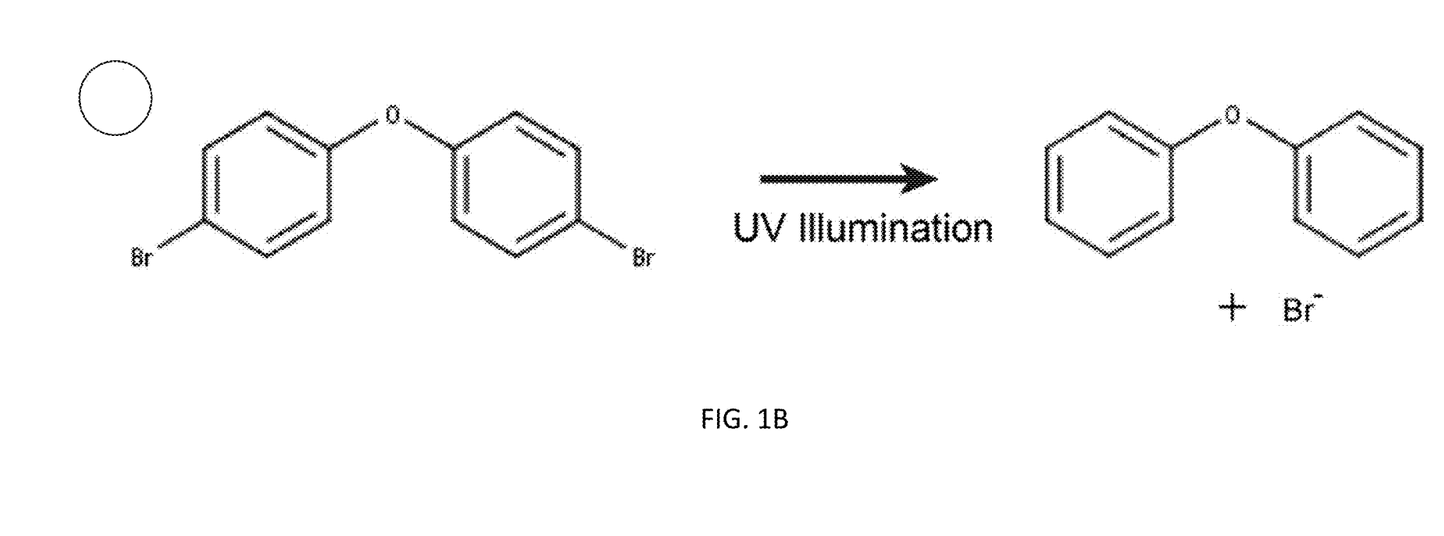
FIG. 1B schematically illustrates a debromination reaction via UV illumination.
Figure 1C:
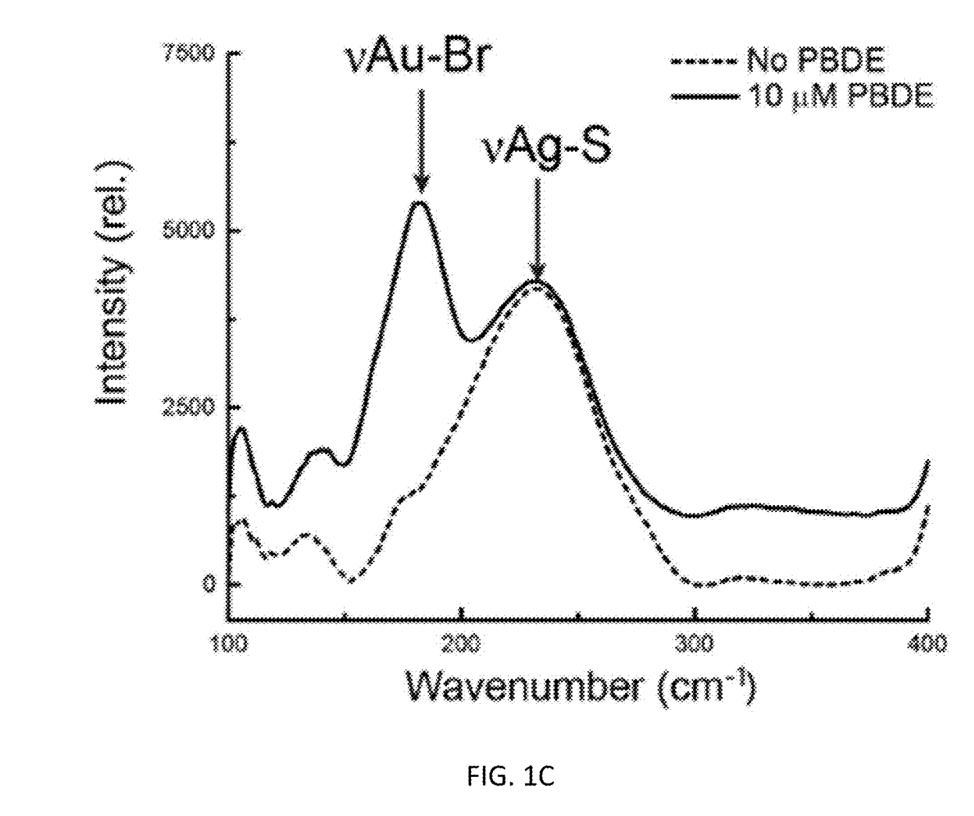
FIG. 1C shows example spectra from an experimental sensor.
Figure 1D:
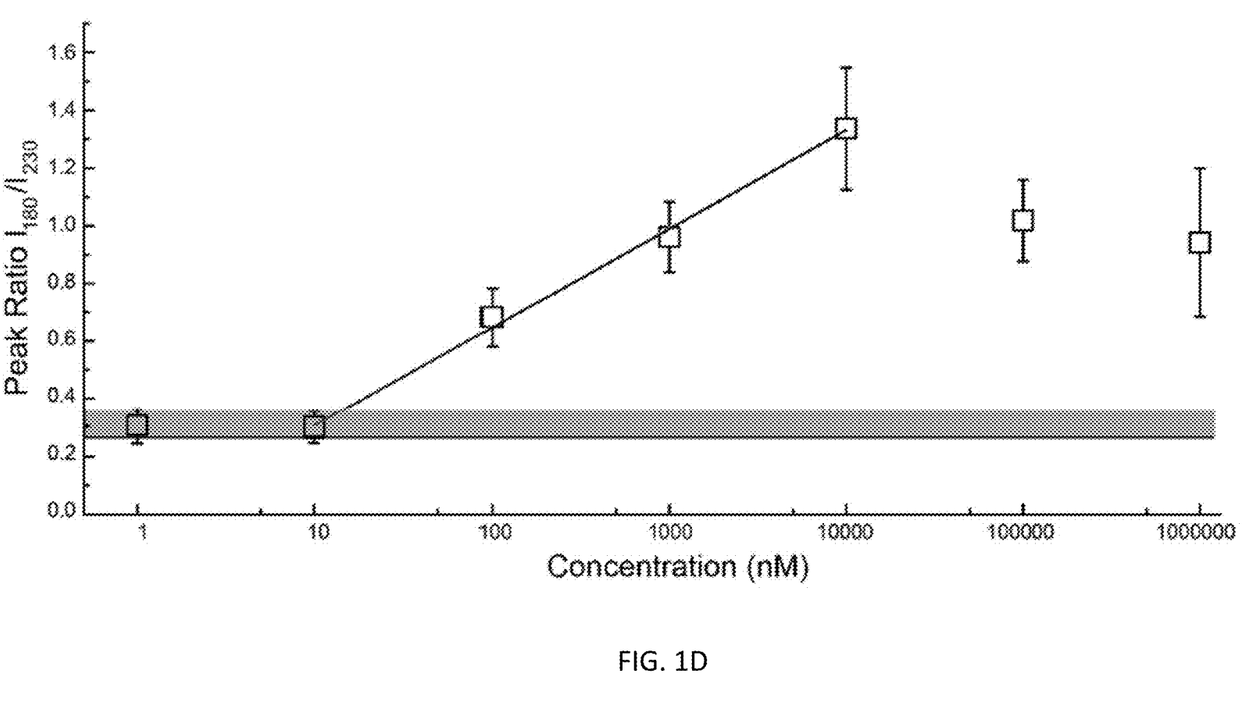
FIG. 1D shows intensity data as a ratio of Au—Br stretch to Ag—S stretch vs concentration of PBDE.

Experiments used an analyte of PBDE, silver nanocubes with a layer of thiophenol, and a gold surface with a layer of Br. In the experiments, the PBDE was first subject to debromination via UV illumination. This reaction schematic is shown in FIG. 1B. Specifically, FIG. 1B shows the molecule bis(4-bromophenyl)Ether (PBDE 15, Sigma-Aldrich) before and after UV illumination. In an experiment, the PDMS stamp was applied after 3 hours of UV illumination. The sensor is then subjected to surface enhanced spectroscopy (SERS) to obtain SERS spectra. The stamp itself performs a role during the SERS sensing in forming the optical cavity. The optical cavity created by the stamp, monolayer and metal surface allows an increase in the Raman signal, which is required for the high sensitivity of analyte detection Example spectra for an Au substrate incubated in a control (EtOH) (dashed line) and 10 uM PBDE 15 (black line) are shown in FIG. 1C, where the spectra are offset for clarity. FIG. 1D shows intensity data as a ratio of Au—Br stretch to Ag—S stretch vs concentration of PBDE. The lower wide band indicates the range of measurements with no PBDE present. The thin sloped line indicates a linear regression.

The experiment for PBDE sensing was carried out as follows. Solutions of concentrations of PBDE 15 varying from 1 nM to 1 mM in ethanol were prepared and a clean Au substrate treated with thiophenol was added to each vial. The samples, along with a prepared Au substrate in ethanol, were incubated under a 254 nm UV lamp for 3 hrs. After incubation the samples were removed and dried and a PDMS (polydimethylsiloxane) stamp with thiophenol functionalized Ag nanocubes was placed on top. Instead of PDMS, other silicon-based materials can be used as a stamp. The stamp material should be optically transparent and should promote adhesion of the nanostructures. Preferentially, the stamp is made of soft material that allows conformal contact with the metal surface. Other specific example materials include epoxy, polystyrene and other polymer films, and hydrogels. SERS measurements were then taken using a 785 nm laser and data taken at 100 points on the surface were averaged. The collected SERS spectra shown in FIG. 1C were taken for an Au substrate incubated in ethanol (dashed line) and spectra taken for an Au substrate incubated in a 10 μM solution of PBDE (black line). A peak is observed at 230 $cm^{-1}$ which is attributed to the Ag—S stretch of the ligand on Ag nanoparticle. In the 10 uM incubated sample a strong peak appears at 180 $cm^{-1}$, consistent with expected values for Au—Br stretch. To quantify the intensity of the peak at 180 we compare the intensity of the peak at 180 to that at 230. FIG. 1D shows a plot of the peak ratio (averaged over 100 points) for measured concentrations. The flat wide line indicates the ratio measured for Au incubated in a solution of ethanol. At the lowest concentrations of 1 and 10 Nm the peak ratios fall within the variation observed with no PBDE present. For the concentrations of 10 nM to 10 μM the ratio of peak intensity increases linearly before the signal begins to fall off with higher concentrations. Using a linear regression of y=−0.039+0.343x (where x is the logarithm of the PBDE 15 concentration and y is the ratio of Au—Br stretch to Ag—S stretch) with the correlation coefficient of 0.996 (FIG. 1D thin line) we estimate a limit of detection of 28 nM (three times above the standard deviation of the blank), which is among the lowest known to the inventors for SERS sensing of PBDEs. Additionally, the spectra show an added benefit of a unique signature that can be detected even in the presence of organic materials that also contain benzene rings.

One advantage provided by the present metasurface enhanced Raman spectroscopy is the ability to modify the surface of either or both of the metallic surface or the plasmonic nanostructures in order to attract analyte molecules. Attracting and confining the analyte molecules provides unprecedented sensitivity compared to traditional SERS substrates. This sensitivity was demonstrated with polybrominated diphenyl ethers (PBDEs).

Figure 2:
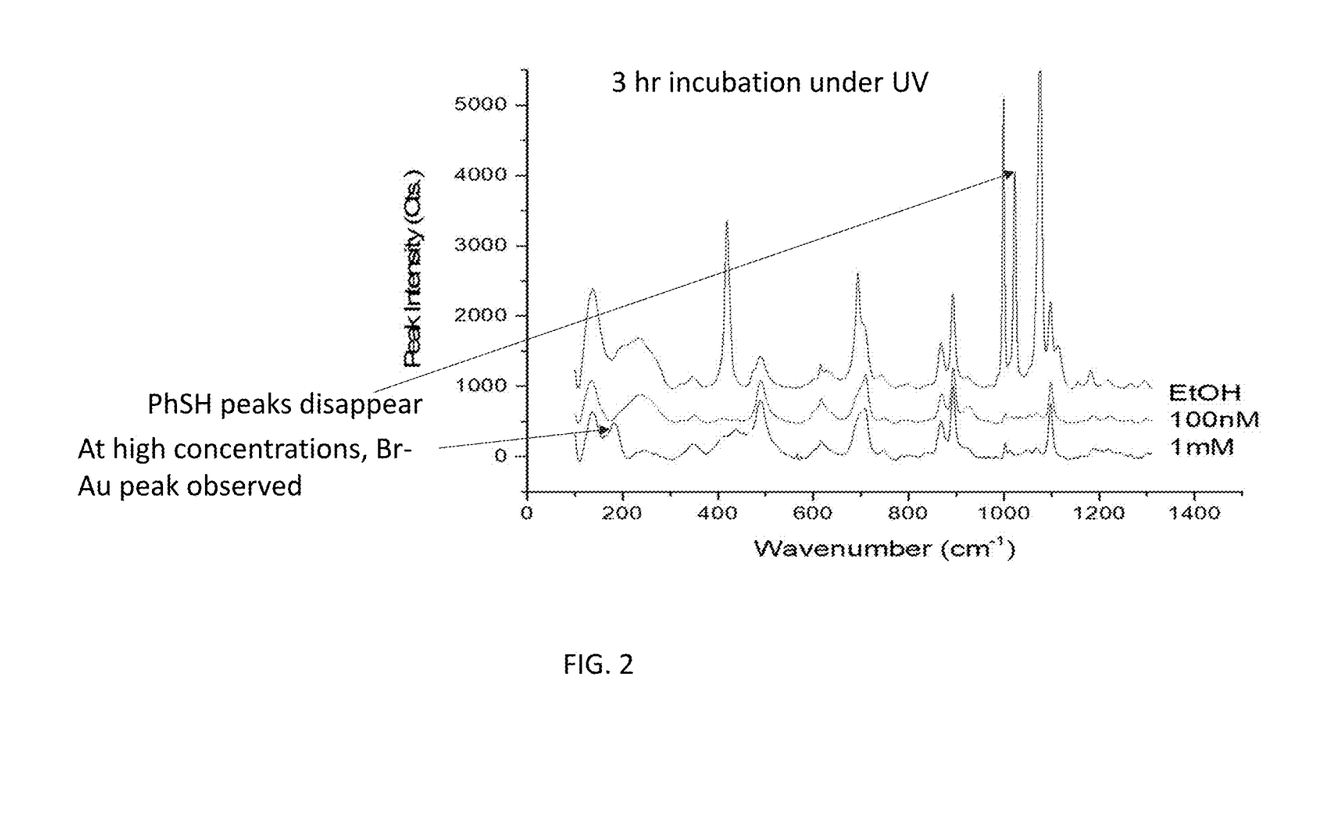
FIG. 2 shows Raman spectra collected after a three-hour incubation of a thiophenol functionalized gold substrate in varying PBDE concentrations under UV illumination.

FIG. 2 shows Raman spectra collected after a three-hour incubation of a thiophenol functionalized gold substrate in varying PBDE concentrations under UV illumination. When incubated in ethanol under UV light, after three hours the characteristic Raman peaks of thiophenol are still present, indicating that the UV illumination does not degrade the thiophenol monolayer. At a concentration of 100 nM, we observe the displacement of thiophenol peaks and at high concentrations, a strong Br—Au peak is observed.

Figure 3A:
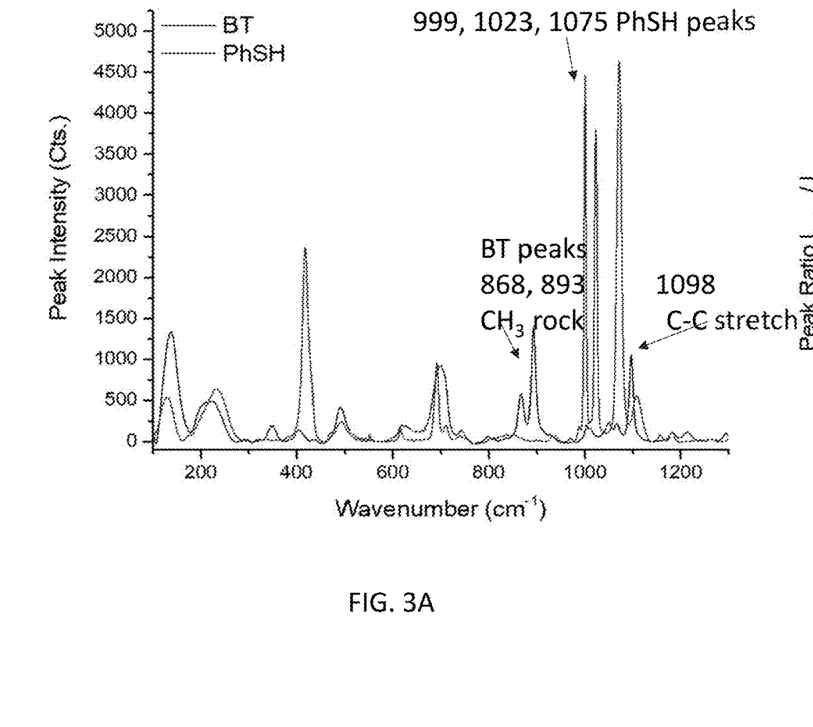
FIGS. 3A and 3B show data collected with nanocubes functionalized with butane thiol.
Figure 3B:
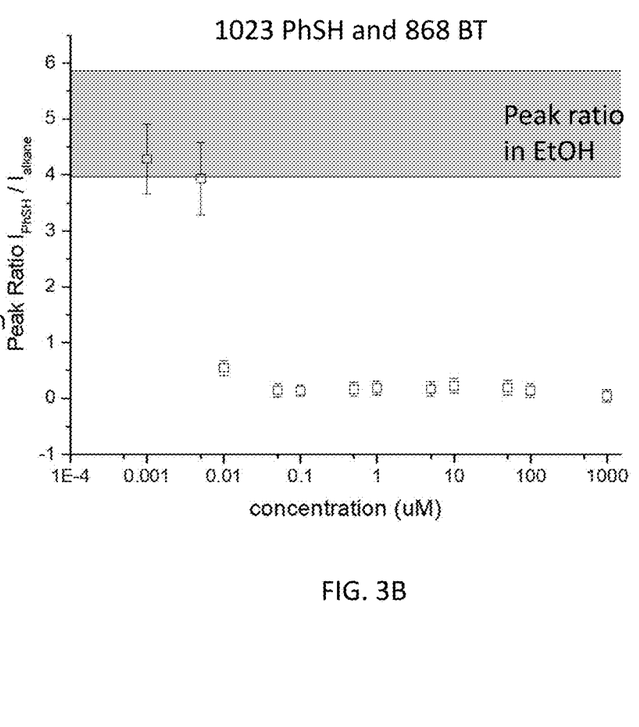

FIGS. 3A and 3B show data collected with cubes functionalized with butane thiol. FIG. 3A shows the Raman spectra for thiophenol and butane thiol. The characteristic peaks are indicated. FIG. 3B shows the ratio of the 1023 thiophenol peak to the 868 butane thiol peak after a thiophenol functionalized gold substrate was incubated in varying concentrations of PBDE solution under UV. The peak ratio after incubation in ethanol is shown in the shaded gray area. We observe that the peak ratio changes dramatically after incubation in at least a 10 nM solution.

Figure 4A:
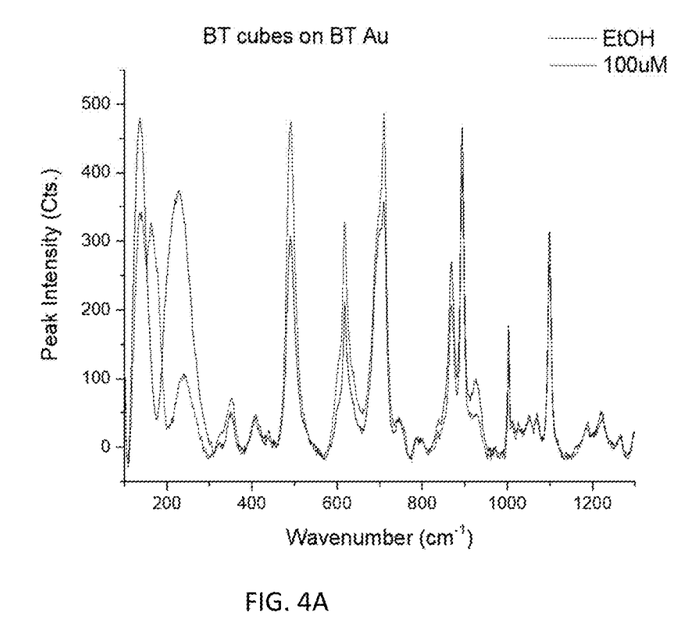
FIGS. 4A and 4B show the spectra collected for butane thiol functionalized gold substrates for 30 minutes under UV illumination.
Figure 4B:
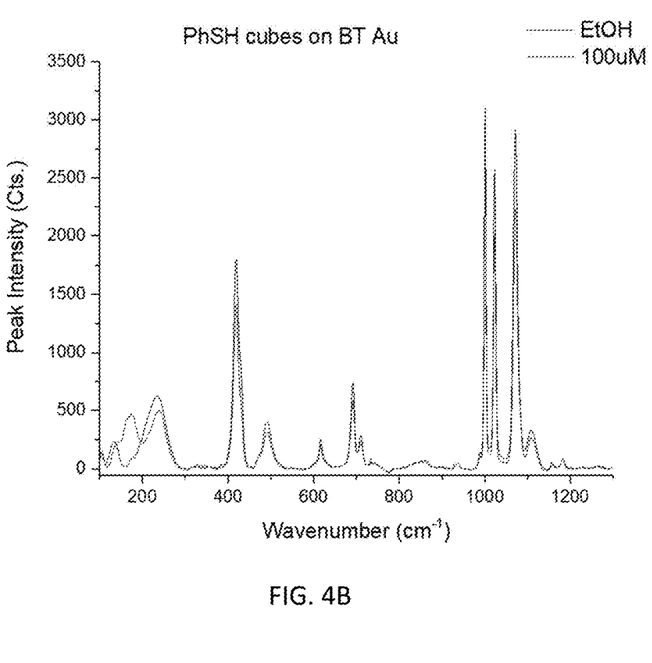

FIGS. 4A and 4B show the spectra collected for butane thiol functionalized gold substrates for 30 minutes under UV illumination. FIG. 4A shows the spectra for a control (ethanol) with 100 uM PBDE solution for butane thiol functionalized cubes. FIG. 4B shows thiophenol functionalized cubes.

Figure 5:
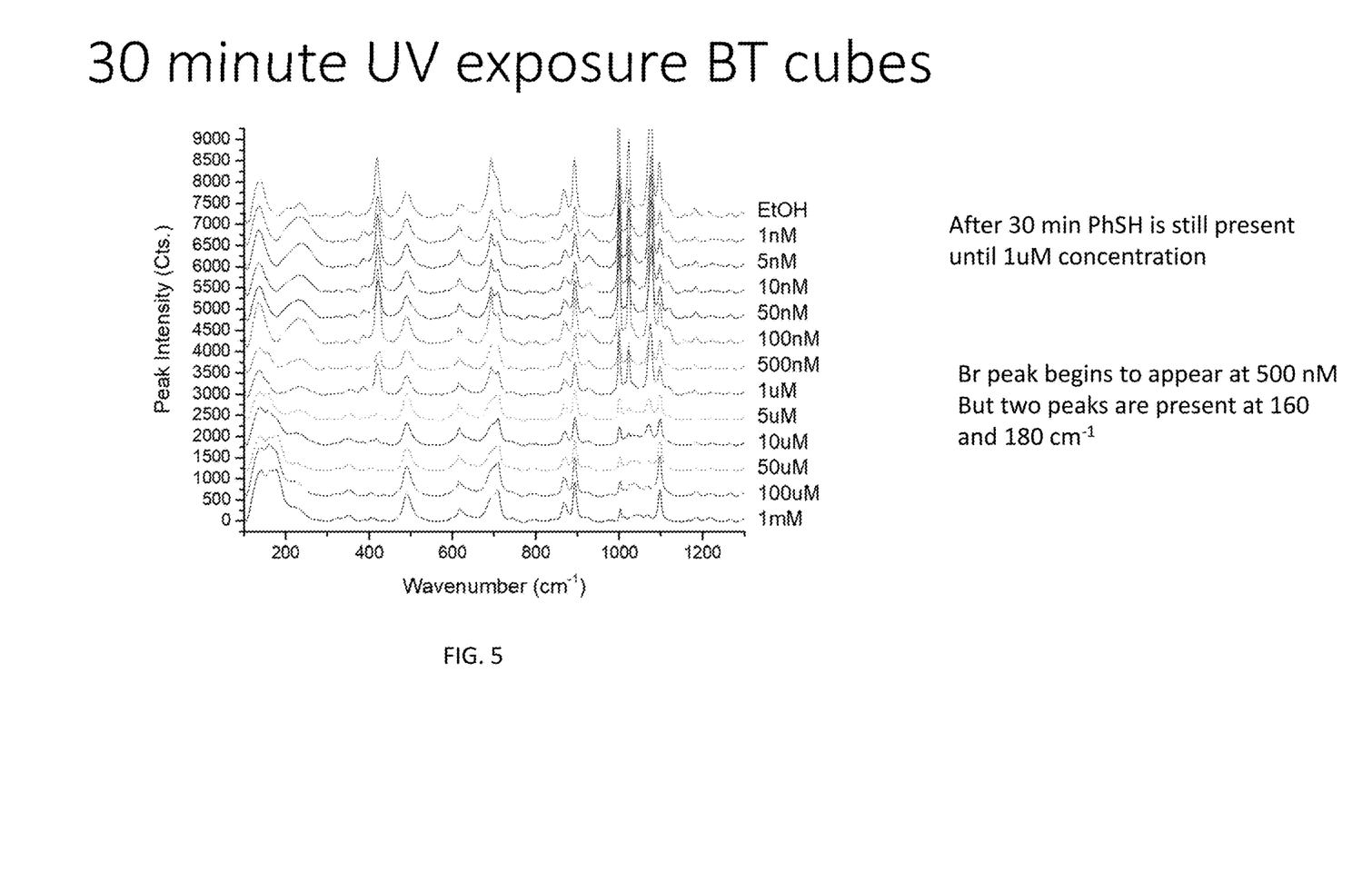
FIG. 5 shows data of a concentration study using a 30 minute UV incubation of thiophenol functionalized gold using butanethiol functionalized nanocubes.

FIG. 5 shows a concentration study using a 30 minute UV incubation of thiophenol functionalized gold using butanethiol functionalized cubes. The thiophenol peaks are present until a concentration of 1 uM, after which the Br—Au peak begins to appear at 500 nM. It is noted that instead of a single Br peak at 180 $cm^{-1}$, a second peak is also present at 160 $cm^{-1}$.

Figure 6A:
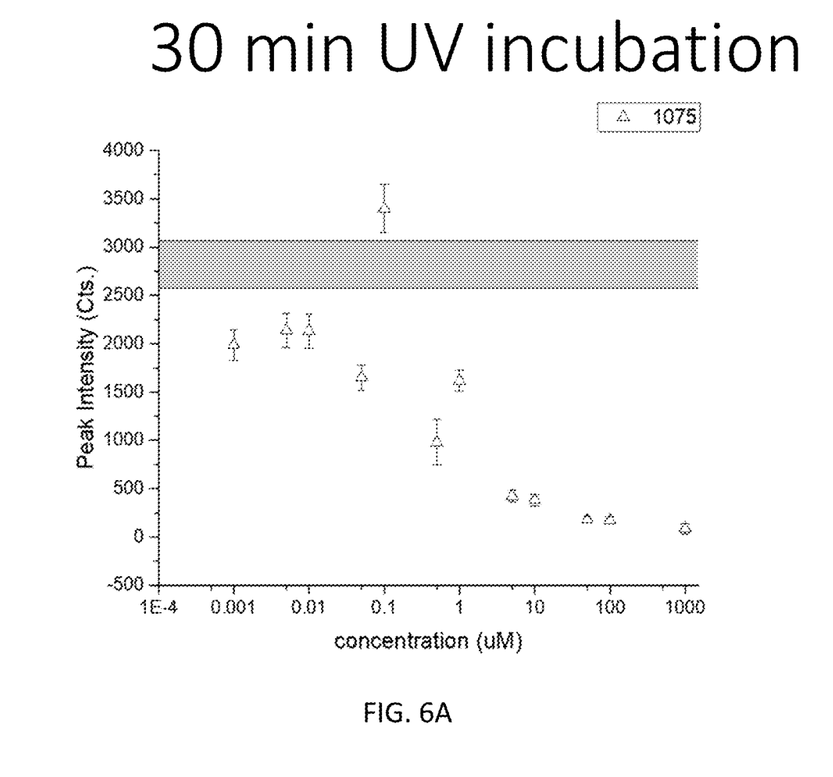
FIGS. 6A-6C show the intensity of characteristic peaks for the 30 min incubation.
Figure 6B:
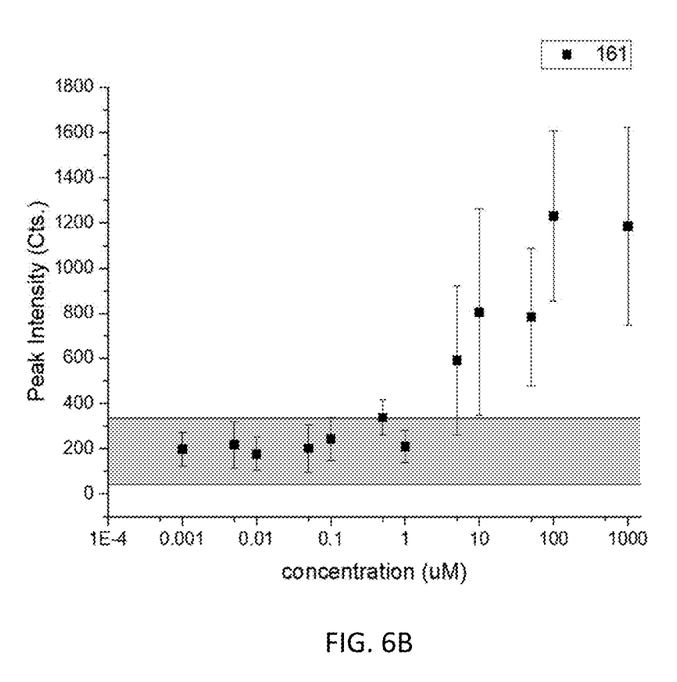
Figure 6C:
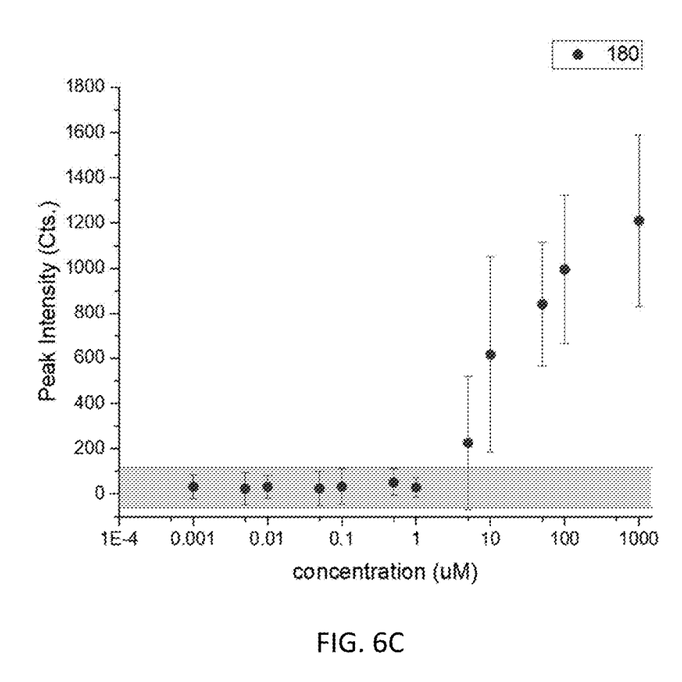

FIGS. 6A-6C show the intensity of characteristic peaks for the 30 min incubation. FIG. 6A shows the 1075 thiophenol peak intensity decreases with higher concentration, but is almost always lower than the peak intensity observed after incubation in ethanol (shaded region). FIGS. 6B and 6C show the peak intensities for both the 161 and 180 peaks. At 5 uM the peak intensity increases above that observed after incubation in ethanol (shaded region).

Figure 7A:
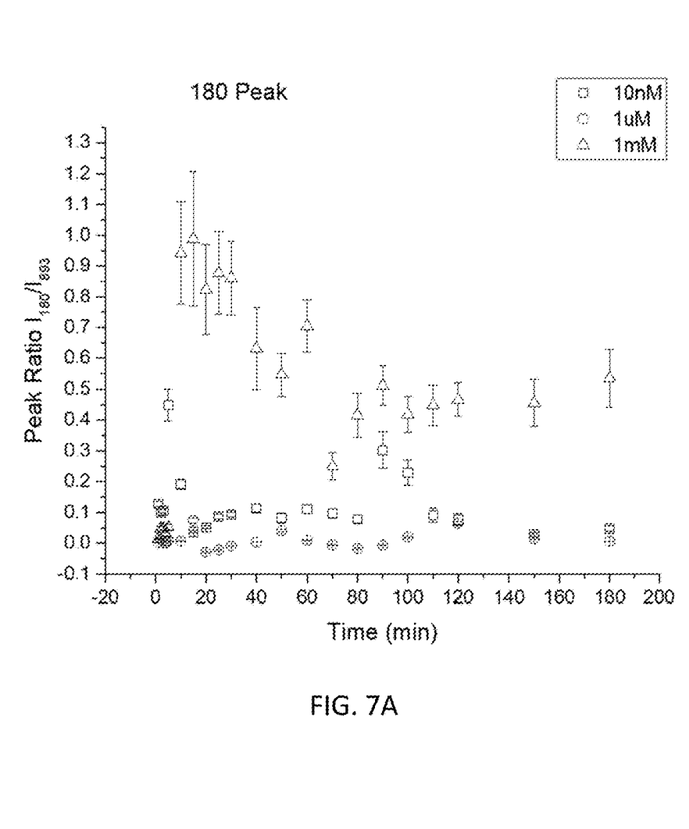
FIGS. 7A & 7B show a kinetic study of thiophenol functionalized gold incubated up to three hours under UV illumination.
Figure 7B:
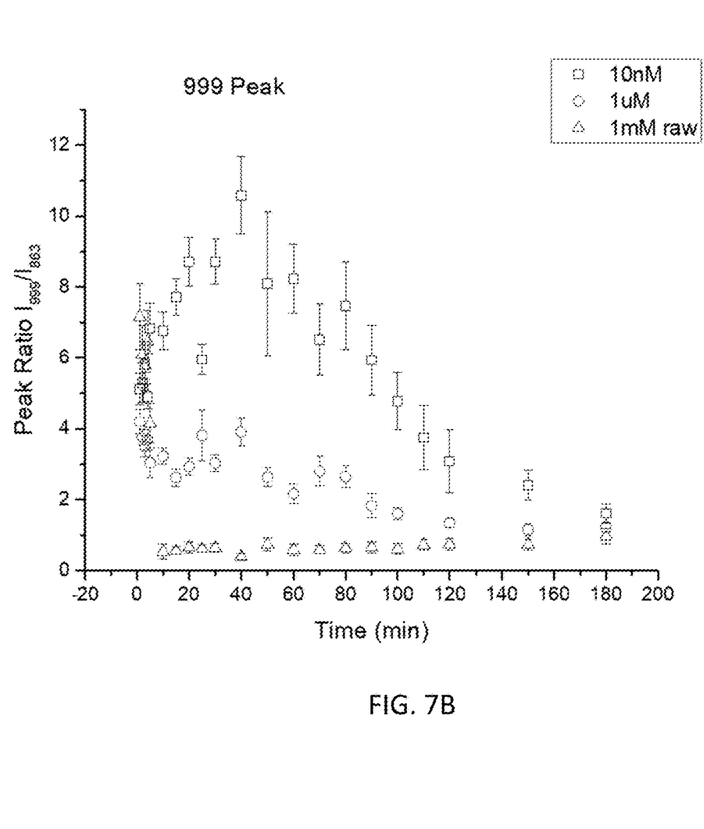

FIGS. 7A & 7B show a kinetic study of thiophenol functionalized gold incubated up to three hours under UV illumination, tested with butanethiol functionalized cubes. FIG. 7A shows the ratio of the 180 cm$^{-1}$ BT peak to the 893 thiophenol peak. The ratio maximizes around 20 minutes and decreases afterward, leveling out a 90 minutes. FIG. 7B shows the ratio of the 999 thiophenol peak to the 863 BT peak. We see the removal of thiophenol at higher concentrations happens after 10 minutes.

Figure 8A:
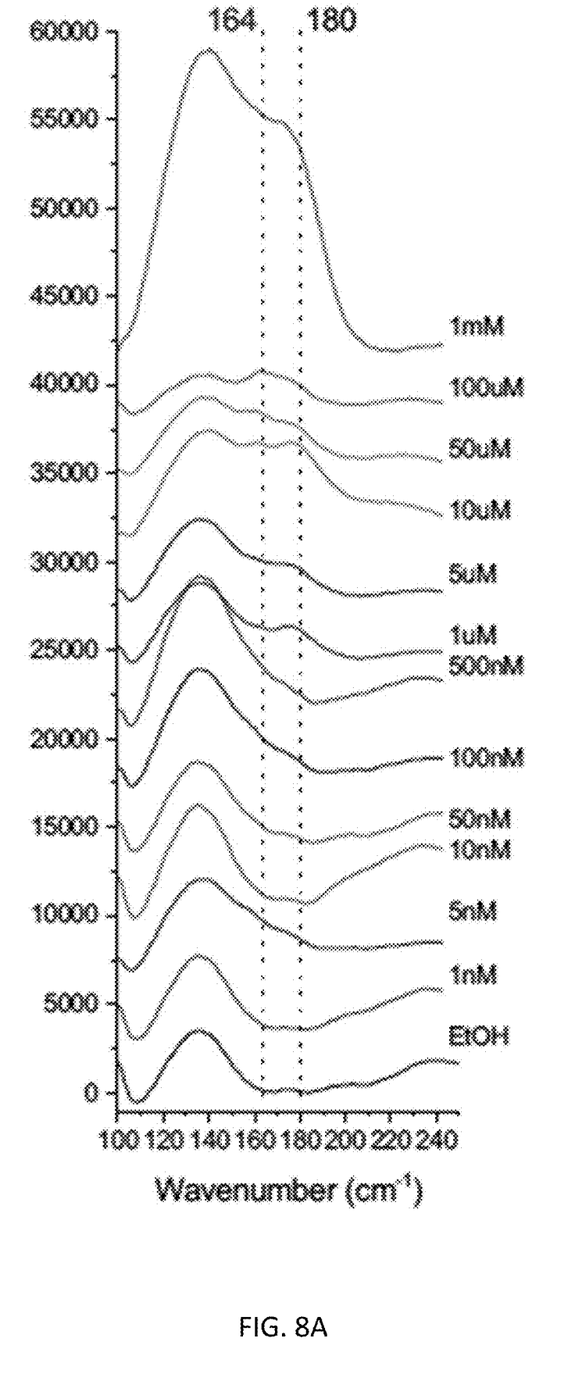
FIGS. 8A-8C show a concentration study after thiophenol functionalized gold was incubated for two hours and measured using butanethiol functionalized nanocubes.
Figure 8B:
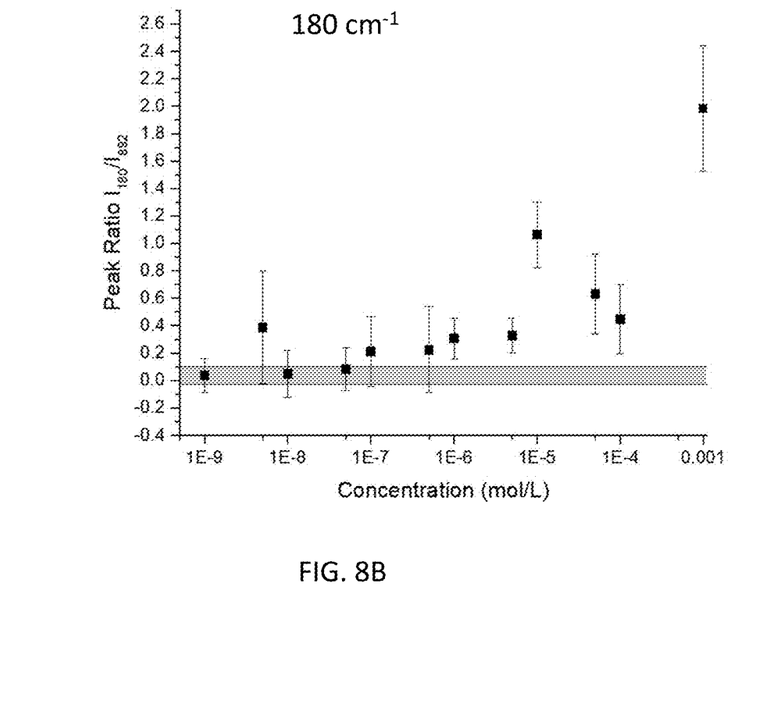
Figure 8C:
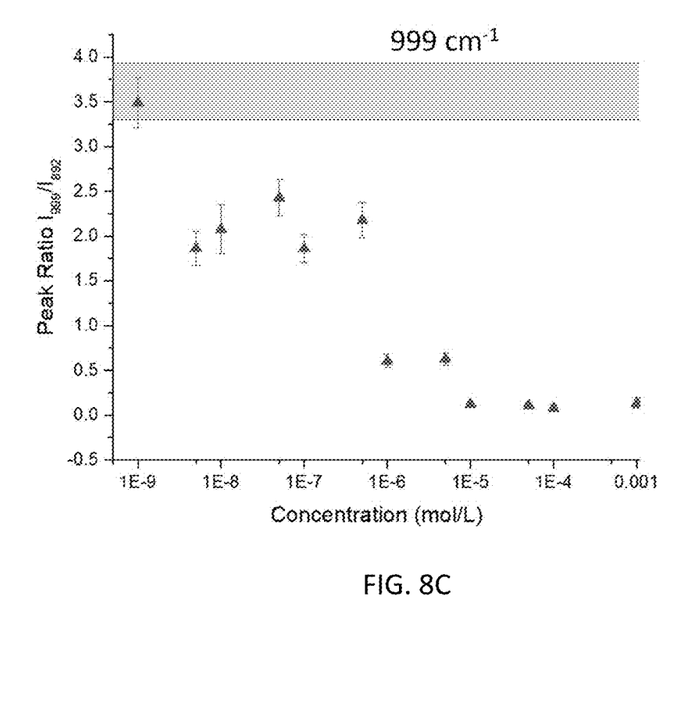

FIGS. 8A-8C show a concentration study after thiophenol functionalized gold was incubated for two hours and measured using butanethiol functionalized cubes. FIG. 8A shows the 180 cm−1 Au—Br peak for various concentrations. FIG. 8B shows the peak ratio for the 180 Br peak to the 892 thiophenol peak. The peak ratio rises above the control measurements (shaded) at a concentration of 100 nM. FIG. 8C shows the peak ratio of the 999 and 892 thiophenol peaks. The presence of PBDE at a concentration of 5 nM was enough to remove the thiophenol after 2 hours.

Figure 9A:
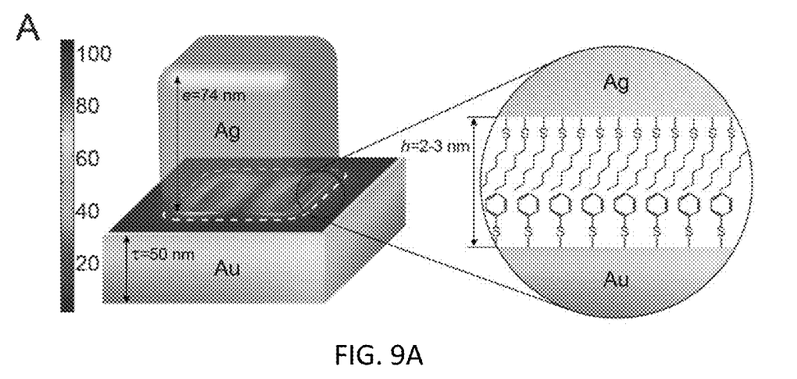
FIG. 9A shows a simulation of the electric field intensity created by the plasmonic resonance of the Au—Ag gap.
Figure 9B:
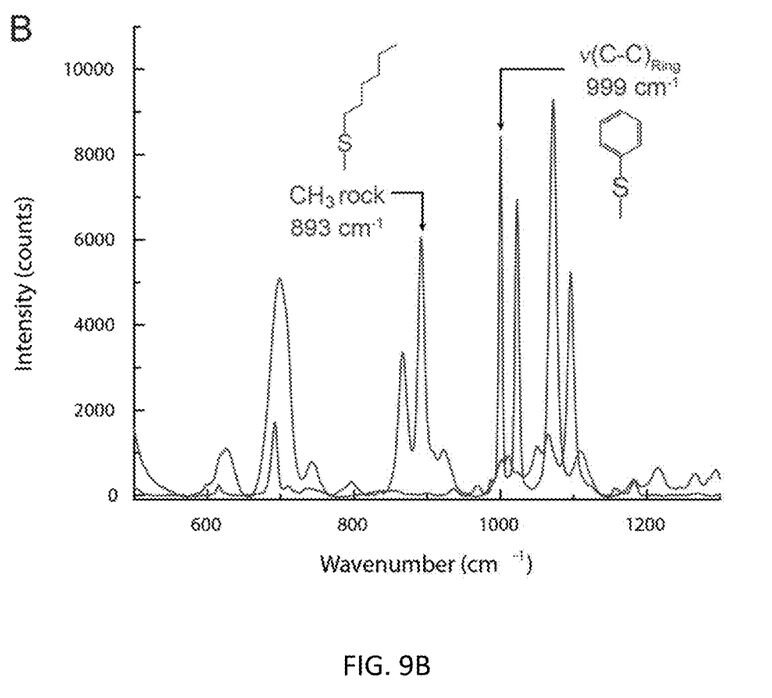
FIG. 9B shows the characteristic Raman spectra for the ligands as used in the analysis.

FIG. 9A shows a simulation of the electric field intensity created by the plasmonic resonance of the Au—Ag gap. The inset shows the monolayer of ligands, thiophenol on Au and butanethiol on Ag. FIG. 9B shows the characteristic Raman spectra for the ligands as used in the analysis.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A chemical analyte sensor, comprising
a monolayer of shaped nanostructures,
a metal or metallized surface,
analyte confined between the monolayer of shaped nanostructures and the metal or metallized surface, wherein the shaped nanostructures and metal surface are selected to provide an optical resonance in an optical cavity defined by them that matches or overlaps with optical excitation of an excitation laser directed at a metasurface formed at the metal or metallized surface, and
a stamp attached to the monolayer that sandwiches the monolayer between the stamp and the metal or metallized surface.

2. The sensor of claim 1, wherein the shaped nanostructures are Ag nanocubes and the metal or metallized surface is a gold surface.

3. The sensor of claim 1, wherein the nanostructures comprise a passivation layer having a known and predetermined Raman vibrational signature configured for subtraction from spectral signatures.

4. The sensor of claim 3, wherein the passivation layer comprises thiophenol.

5. The sensor of claim 1, wherein one or both of the metal or metallized film or the shaped nanostructures is functionalized to attract molecules of the analyte.

6. The sensor of claim 1, wherein the shaped nanostructures comprise nanocubes.

7. The sensor of claim 1, wherein the shaped nanostructures comprise nanodisks, nanoprisms, nanosheets, nanoribbons, nanopyramids, nanospheres, or nanorods.

8. The sensor of claim 1, wherein the metal or metallized surface comprises one of Ag, Fe, Ni, Pt, and Cu.

9. The sensor of claim 1, wherein the stamp comprises polydimethylsiloxane.

10. The sensor of claim 1, wherein the stamp comprises an optically transparent silicone-based material.

11. The sensor of claim 1, wherein the stamp is made of soft material that allows conformal contact of the shaped nanostructures with the metal surface.

12. The sensor of claim 1, wherein the stamp comprises epoxy or polystyrene.

13. The sensor of claim 1, wherein the stamp comprises a polymer film.

14. A method for detecting an analyte, comprising:
coating a stamp with a monolayer of shaped nanostructures,
confining the analyte in an optical cavity formed between the monolayer of shaped nanostructures and a metal or metallized surface by applying the stamp to the metal or metallized surface,
subjecting the metasurface formed at the metal or metallized surface to laser excitation that overlaps with or matches an optical resonance of the metasurface,
taking data from a plurality of points on the metasurface, and
analyzing the data via surface enhanced spectroscopy to detect whether a peak associated with the analyte is present.

15. The method of claim 14, wherein the analyte is polybrominated diphenyl ethers, and the method comprises initially subjecting the analyte to UV light to form a Br radical that bonds to the metal or metalized surface.

16. The method of claim 15, further comprising sandwiching the Br radical between the monolayer of shaped nanostructures and the metal or metallized surface.

17. The method of claim 16, wherein the stamp comprises a soft and transparent polymer film.

18. The method of claim 14, wherein the stamp comprises a soft and transparent polymer film.

* * * * *